United States Patent
Rongen et al.

(10) Patent No.: US 9,478,018 B2
(45) Date of Patent: Oct. 25, 2016

(54) MULTIFUNCTIONAL INTERFACE FOR MEDICAL IMAGING

(71) Applicant: KONINKLIJKE PHILIPS N.V., Eindhoven (NL)

(72) Inventors: Peter Maria Johannes Rongen, Eindhoven (NL); Fransciscus Johannes Leonardus Everaerts, Weert (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 42 days.

(21) Appl. No.: 14/402,582

(22) PCT Filed: Jun. 13, 2013

(86) PCT No.: PCT/IB2013/054842
§ 371 (c)(1),
(2) Date: Nov. 20, 2014

(87) PCT Pub. No.: WO2013/190433
PCT Pub. Date: Dec. 27, 2013

(65) Prior Publication Data
US 2015/0235354 A1 Aug. 20, 2015

Related U.S. Application Data

(60) Provisional application No. 61/661,978, filed on Jun. 20, 2012.

(51) Int. Cl.
| | |
|---|---|
| G06K 9/00 | (2006.01) |
| G06T 7/00 | (2006.01) |
| A61B 6/00 | (2006.01) |
| G01N 23/04 | (2006.01) |
| A61B 5/05 | (2006.01) |

(52) U.S. Cl.
CPC ....... *G06T 7/00* (2013.01); *G06T 2207/10004* (2013.01); *G06T 2207/10116* (2013.01); *G06T 2207/30008* (2013.01)

(58) Field of Classification Search
CPC .................................. G06T 7/00; A61B 6/00
USPC ....... 382/128, 129, 130, 131, 132, 133, 134; 378/4, 8, 21–27, 901; 600/407, 410, 600/411, 425, 427
See application file for complete search history.

(56) References Cited

U.S. PATENT DOCUMENTS

| | | | |
|---|---|---|---|
| 4,993,404 A | 2/1991 | Lane | |
| 5,416,819 A * | 5/1995 | Uzuyama | A61B 6/4225 378/114 |
| 5,883,615 A * | 3/1999 | Fago | A61B 6/0457 200/86.5 |
| 2007/0269011 A1 | 11/2007 | Sandkamp et al. | |
| 2008/0284725 A1 | 11/2008 | Logue | |
| 2011/0013005 A1 | 1/2011 | Watkins | |
| 2011/0060423 A1* | 3/2011 | Bonfiglio | A61B 6/00 700/11 |
| 2011/0267465 A1 | 11/2011 | Alexander et al. | |

OTHER PUBLICATIONS

Bredno et al, "Algorithmic Solutions for Live Device-To-Vessel Match", In Proceedings of SPIE—vol. 5370—Medical Imaging 2004: Image Processing, May 2004, pp. 1486-1497.

* cited by examiner

*Primary Examiner* — Abolfazl Tabatabai

(57) ABSTRACT

A multifunctional interface for medical imaging has a lower limb operable multifunctional interface which includes at least one activation element, such as a foot switch pedal, a timing unit, and a control unit. The activation element is configured to provide an activation signal to the control unit when being activated. Further, the timing unit is configured to provide a timing signal to the control unit upon being provided with the activation signal from the activated activation element. The control unit is configured to provide at least two different control signals for triggering at least two different predetermined actions. Further, the control signal is dependent on a duration of the timing signal.

20 Claims, 4 Drawing Sheets

MULTIFUNCTIONAL INTERFACE FOR MEDICAL IMAGING

CROSS-REFERENCE TO PRIOR APPLICATIONS

This application is the U.S. National Phase application under 35 U.S.C. §371 of International Application Serial No. PCT/IB2013/054842, filed on Jun. 13, 2013, which claims the benefit of U.S. Application Ser. No. 61/661,978, filed on Jun. 20, 2012. These applications are hereby incorporated by reference herein.

FIELD OF THE INVENTION

The present invention relates to multifunctional interfaces for medical imaging, and relates in particular to a lower limb operable multifunctional interface, medical imaging device, an X-ray imaging system and a method for controlling an X-ray imaging system, as well as to a computer program element and a computer readable medium.

BACKGROUND OF THE INVENTION

In medical imaging, for example during a treatment of a patient, interfaces for user interaction are provided. For example, footswitches are provided in order to activate X-ray imaging. Further, manually operable user interfaces, such as table side modules, are provided for the physician to activate navigation tools. For example, in case of coronary artery syndrome treatments, where X-ray imaging is used for diagnosing, navigating and treating a coronary stenosis, a physician is assisted in navigation of a guide wire through a diseased coronary artery. For example, a previously recorded angiogram can be overlaid, providing cardiac roadmapping overlaid onto a life fluoroscopy image that only shows the guide wire and its radiopaque tip. The table side module may be attached to the patient table and provides a touchscreen with buttons and messages guiding the physician through the use of the application. However, the need to press or activate buttons on a screen may be cumbersome due to the limited range of reach of the physician's arm. US 2011/0060423 A1 describes automatic activation and deactivation of a radiation source for medical purposes and describes an observation whether the eyes of the user face a point of reference or not, thus ensuring that X-ray radiation is only provided on purpose. The user is provided with a receiver or emitter, and the monitor is provided with the respective counterpart emitter or receiver, such that a signal is only generated when the operator is looking at the monitor or in the appropriate direction.

SUMMARY OF THE INVENTION

However, it has been shown that despite the achievable monitoring function, this requires a certain behaviour pattern of the user.

Thus, there may be a need to provide a facilitated and thus easier to operate interface for a medical X-ray imaging system.

The object of the present invention is solved by the subject-matter of the independent claims, wherein further embodiments are incorporated in the dependent claims.

It should be noted that the following described aspects of the invention apply also for the lower limb operable multifunctional interface, the medical imaging device, the X-ray imaging system, the method for controlling an X-ray imaging system, the computer program element and the computer readable medium.

According to a first aspect of the present invention, a lower limb operable multifunctional interface is provided, comprising at least one activation element, a timing unit, and a control unit. The activation element is configured to provide an activation signal to the control unit when being pressed. The timing unit is configured to provide a timing signal to the control unit upon being provided with the activation signal from the pressed activation element. The control unit is configured to provide at least two different control signals for triggering at least two different predetermined actions. The control signal is dependent on the duration of the timing signal.

Based on the timing signal, a respective selection is made such that one of the control signals is chosen to be sent or provided for further activation or action triggering purposes. The choice of the control signal is thus depending on the duration of the timing signal.

Instead of providing an activation element that can be pressed for activation, the vice versa can be provided in form an activation element that is being pulled for activation.

The lower limb operable multifunctional interface may be operable by the user's feet or knees.

According to an exemplary embodiment, the lower limb operable multifunctional interface is a foot operable interface and the activation element is provided as a pedal.

According to an exemplary embodiment, a first control signal is provided upon pressing the activation element for a first duration, and a second control signal is provided upon pressing the activation element for a second duration. For example, the first duration is longer than the second duration. The threshold value, i.e. the minimum value for the first duration, is approximately 500 milliseconds. In another example, a threshold value of one or more seconds is provided, for example 2 or 5 seconds.

In another example, as a parameter for determining the time or duration, the timing device is provided for counting incoming images, for example, when providing a switch for activating fluoroscopy images. For example, the threshold value for differentiating between the first and the second duration is five images.

According to an exemplary embodiment, the at least two different control signals are provided to activate different functions of a medical imaging system. A first control signal is provided controlling a first function, and a second control signal is provided to activate a second function. The first function comprises X-ray image acquisition, and the second function comprises an activation and/or deactivation of a predetermined display mode.

For example, the predetermined display mode comprises a cardiac navigation application providing navigation aids, for example comprising an overlay of an X-ray image with a vessel roadmap based on or several previous images. The vessel roadmap may comprise an angiogram.

According to an exemplary embodiment, two or more activation elements are provided, wherein at least two of the activation elements are each configured to provide different control signals dependent on the duration of the pressing of the respective activation element.

According to a second aspect of the present invention, a medical imaging device is provided, comprising an image processing unit, a display unit, and an interface unit. The image processing unit is configured to generate at least first and second image data. The display unit is configured to display the at least first and second image data. The interface unit is provided as a lower limb operable multifunctional interface according to one of the preceding examples. The image processing unit is configured to provide the at least first and second image data to the display unit depending on the at least two different control signals provided by the interface unit.

The processing unit may be configured to have image data stored thereon.

According to a third aspect of the present invention, an X-ray imaging system is provided, comprising an X-ray image acquisition unit, a processing unit, a display unit, and a control interface. The X-ray image acquisition unit comprises an X-ray source, an X-ray detector, and is configured to acquire X-ray image data. The processing unit is configured to generate medical image data. The display unit is configured to present the medical image data. The control interface is provided as a lower limb operable multifunctional interface according to one of the above mentioned examples.

The lower limb operable multifunctional interface provides a first control signal to activate a first function, and a second control signal to activate a second function. The first function comprises an X-ray image acquisition, and the second function comprises an activation and/or deactivation of a display mode.

According to an exemplary embodiment, a graphical user interface is provided showing different activation areas for controlling different functions. The different functions relate to the at least two different signals of the lower limb operable multifunctional interface.

According to a fourth aspect of the present invention, a method for controlling an X-ray imaging system is provided, comprising the following steps:
  a) generating an activation signal by pressing an activation element;
  b) providing a timing signal upon being provided with the activation signal;
  c) providing at least two different control signals for triggering at least two different predetermined actions dependent on the duration of the timing signal. The activation element is a lower limb operable interface, for example operable by the user's feet or knees.

According to an aspect of the present invention, a lower limb operable switch is provided, added by at least one additional function, thus providing a multifunctional interface or multifunctional switch, by considering the duration of pressing the activation element, for example a pedal. Thus, a delay is incorporated into a foot switch, for example by software means. Thus, for example, by pressing and quickly releasing, a signal can be provided for disabling or enabling a certain event or action. For example, based on certain criteria, a vessel overlay can be switched off or on, and normal intervention images can be shown without overlay or with overlay. By repeating the pressing and quickly releasing, the multifunctional switch can activate the overlay again, i.e. by repeating the pedal action, the overlay can be switched on again. The software may comprise a simple delay timing device, to decide whether the pedal has been released quickly enough, i.e. if the action happened within a certain amount of time, upon which an event is triggered, i.e. a certain predetermined action is activated. Instead of the amount of time, as another criterion the number of possible captured images can be counted when pressing the pedal, for example when providing the pedal also for activating an X-ray acquisition, for example when using low dose X-ray acquisition, when the pedal is also called a fluoroscopy pedal. Upon counting, a disabled action can be performed if the length of the sequence is less than, for example, five frames, or ten frames or other numbers. Upon exceeding a certain amount of time, or frames that possibly would have been captured in the same time, the other function can be activated, for example starting an X-ray beam and providing images that can be viewed on a monitor. The software delay can also be referred to as a virtual delay incorporated into the pedal switch.

According to another aspect of the present invention, a graphical user interface can be provided, for example on the table side module or on a desktop computer. The graphical user interface can be augmented with buttons that carry the same disable/enable actions, as the behaviour of these buttons is synchronized with any disabling or enabling action raised by the multifunctional pedal, for example. Thus, in addition to the lower limb operation, the desired action can also be performed manually, for example by an assistant. For example, the graphical user interface can be provided such that a selection out of a plurality of functions can be chosen and assigned to the multifunctional pedal, for example depending on the state of intervention. For example, during an initial state of the intervention, certain additional features are helpful for the surgeon, such that these are activatable by the multifunctional pedal during the first phase of an operation. In case that different actions are helpful during a further part of the operation or intervention, different functions could be reassigned as the additional functions activatable by the multifunctional pedal. Since the physician's foot is usually always near the pedal, for example near a so-called fluoroscopy pedal, since this is one of the more important instruments, an easy and facilitated way of controlling further navigation aids can be provided. Thus, the multifunctional interface provides the same user interface component that changes the response upon different usage.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
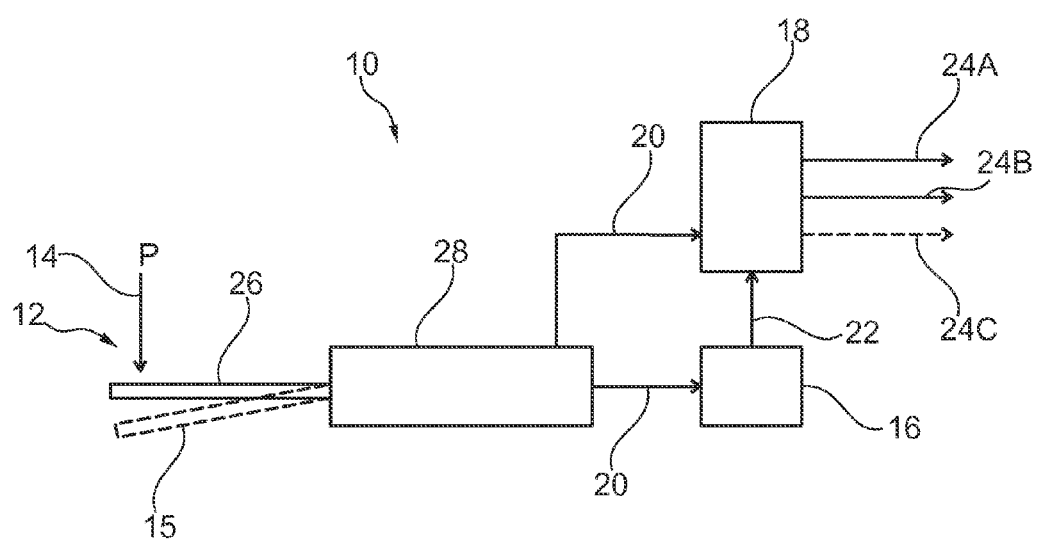
FIG. 1 shows an example of a lower limb operable multifunctional interface in a schematic setup.

FIG. 1 shows a lower limb operable multifunctional interface 10, comprising at least one activation element 12. The lower limb operable multifunctional interface is operable, for example, by a user's feet or knees. For the operation by the user's knees, the activation element 12 is provided to be attachable to a patient support structure, or other suitable structural elements to which the activation element can be temporarily mounted such that a user can press the activation element by a simple sidewards oriented movement of the knee, for example when sitting on a chair next to the patient. It must be noted that in the following, the activation element 12 is described as being able to be pressed for activation. Of course, also a pullable activation element 12 is provided, if such pulling action is considered to be more suitable by the user.

As an example, the activation element 12 is provided as a pedal, as shown in FIG. 1. An arrow 14 indicates activation force P. A dotted structure 15 indicates the possibility to press the activation element 12 for activation.

Further, a timing unit 16 and a control unit 18 are provided in data connection with the activation element 12. The activation element 12 is configured to provide an activation signal 20 to the control unit 18 when being pressed. Further, a respective activation signal 20 is also provided to the timing unit 16, which is configured to provide a timing signal 22 to the control unit 18 upon being provided with the activation signal 20 from the pressed activation element 12. The control unit 18 is configured to provide at least two different control signals 24, for example 24*a* and 24*b* for triggering at least two different predetermined actions, not further shown. The control signal 24 is dependent on the duration of the timing signal 22.

The activation element 12, as shown in FIG. 1, may thus be provided as a pedal. For example, a pedal element 26 is movably mounted to a support or body structure 28. Thus, the foot operable interface 10 may be referred to as foot switch, provided as a multifunctional activation device. The activation element, e.g. the pedal, is also referred to as a pressure time-dependent multifunctional activation element, or pressure time-dependent multifunctional pedal.

The term "pressing of the activation element" may refer to a predetermined minimum pressing width or pressing depth, i.e. the timing signal starts when the activation element is activated such that a threshold amount is exceeded, or reached.

For example, the term "pressing of the activation element" refers to a maximum pressing state, i.e. a state where the activation element cannot be pressed further, i.e. when the activation element has reached a limit stop or a limit position. In such case, the timing signal starts when the activation element is pressed completely.

For example, a first control signal, for example the control signal 24*a*, is provided upon pressing the activation element for a first duration, and a second control signal, for example the control signal 24*b*, is provided upon pressing the activation element for a second duration. The first duration may be defined to be longer than the second duration.

The threshold value, i.e. the minimum value for the first duration is approximately 500 milliseconds, according to an example. In another example, a threshold value of one second, 2 seconds, or 5 seconds, or even longer time period is defined.

The timing, i.e. determination of the duration can be measured based on time as a parameter.

The timing can also be measured based on a time between the starting of the pressing action until the other endpoint of the pressing movement of the pedal, for example, has been reached.

For example, a fast pressing action leading to a short pressing procedure time, can activate the second action, and a slow pressing action can activate the first action, i.e. two different switches—or switching modes—are provided by the same switch, but by different switching action.

In another example, upon reaching the pressing endpoint, a further duration can be timed to provide a second duration; a third duration could be defined as a) a time from the first starting point, or b) a time from the endpoint, i.e. the second starting point.

In another example, as a parameter for determining the time or duration, the timing device is provided for counting incoming images, for example, or for counting possible incoming images, when providing a switch for activating fluoroscopy images. For example, the threshold value for differentiating between the first and the second duration is five images, ten images or another predetermined value.

The at least two different control signals are provided to activate different functions of a medical imaging system (not further shown in FIG. 1). For example, a first control signal is provided controlling a first function in form of an X-ray imaging acquisition. A second control signal is provided to activate as a second function the activation and/or deactivation of a predetermined display mode. For example, the controlling of the second function comprises an activation or deactivation of a cardiac navigation application, providing navigation aids. For example, the predetermined display mode comprises an overlay of an X-ray imaging with a vessel roadmap based on previous images. The vessel roadmap may comprise an angiogram.

Thus, the control unit 18 may provide a delay unit (not further shown) that provides the first control signal upon pressing the activation element, e.g. the pedal, for a first duration and the second control signal upon pressing the activation element/pedal for a second duration. It may also be provided that the second function is provided for a predefined time frame. For example, an overlay may be provided that disappears after a predetermined number of seconds.

According to a further example, also shown in combination with FIG. 1, but not meaning to represent a necessary feature for the above described examples, a third control signal 24*c*, indicated with a dotted arrow, is provided upon pressing the activation element for a third duration.

Also more than three actions can be provided for more than three durations. However, a large number of durations will also result in higher requirements for the pressing skill of the user concerning the pressing of the activation element.

The second signal may activate the predetermined display mode and the third signal may deactivate the predetermined display mode.

The deactivation of the display mode may also be provided by a further second signal instead of the third signal.

According to a further example, not further shown, two or more activation elements are provided, and at least two of the activation elements are each configured to provide different control signals dependent on the duration of the pressing of the respective activation element.

Thus, several multifunctional activation elements can be combined in a foot operable multifunctional interface, e.g. a foot switch multifunctional interface. Thus, at least four different predetermined actions can be activated by the user. For example, one timing unit is provided for several activation elements. In another example, a timing unit is provided for each of the activation elements with a multifunction.

The control unit 18 may be configured to provide an activation signal for X-ray image acquisition when the activation element is pressed for a time period longer than a predetermined time. The control unit 18 is further configured to provide a display mode change signal for changing between at least two different display modes when the activation element is pressed for a time period shorter than a predetermined time.

For example, a threshold value for X-ray imaging and the activation of a certain display mode is 500 milliseconds, after which the X-ray image acquisition procedure may start.

Figure 2:
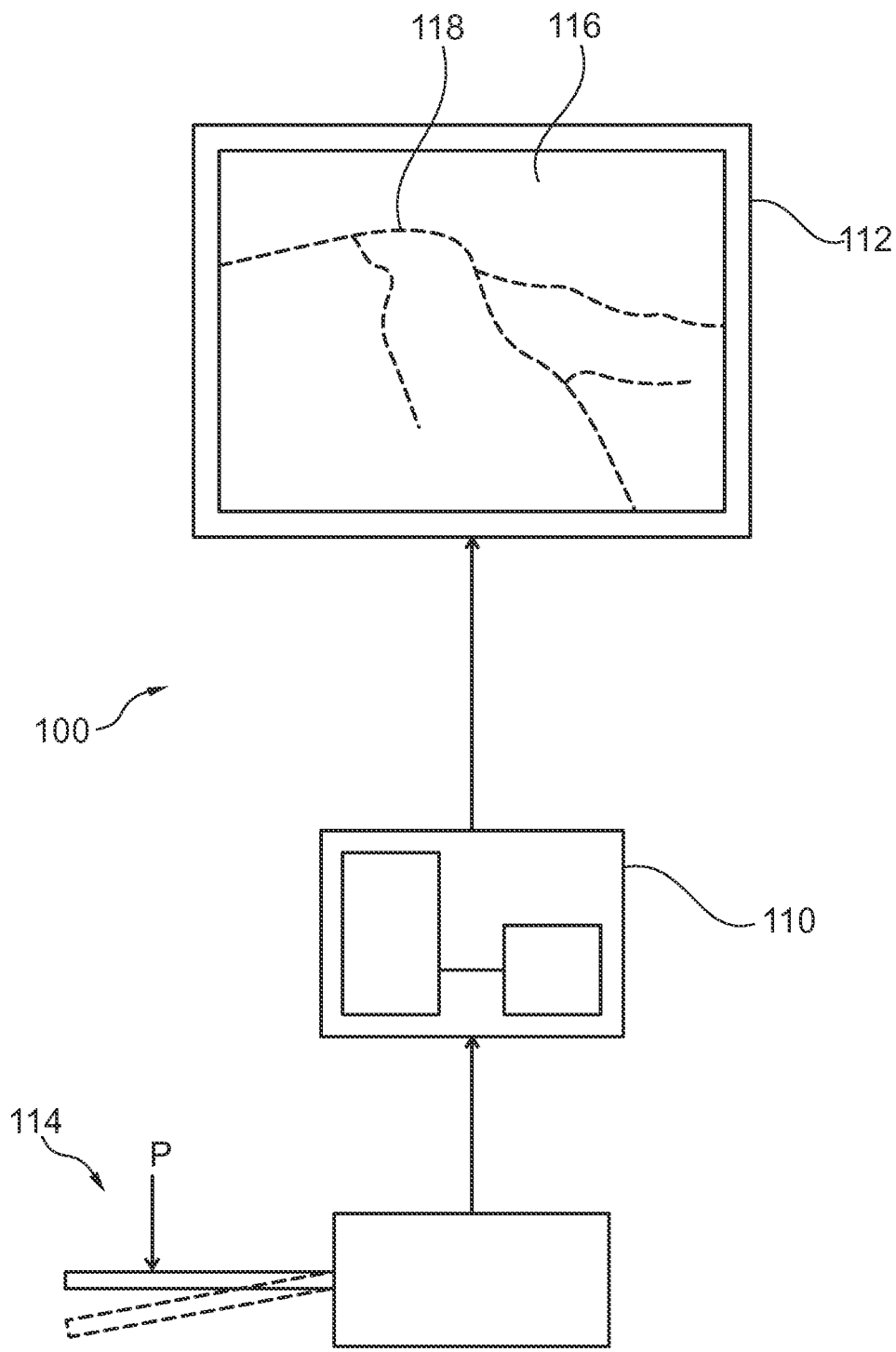
FIG. 2 shows an example of a medical imaging device in a schematic setup.

FIG. 2 shows a medical imaging device 100 comprising an image processing unit 110, a display unit 112, and an interface unit 114. The image processing unit 110 is configured to generate at least first and second image data. Also, image data can be stored. The display unit 112 is configured to display the at least first and second image data. The interface unit 114 is provided as a lower limb operable multifunctional interface according to one of the above mentioned examples, for example the lower limb operable multifunctional interface 10 of FIG. 1. The image processing unit 110 is configured to provide the at least first and second image data to the display unit depending on the at least two different control signals provided by the interface unit.

For example, an X-ray image 116 is shown on the display unit 112 (not further shown in detail due to the gray scale values of X-ray images usually provided, thus representing the first image data). For example, the first image data may be provided as an X-ray image of an object, e.g. fluoroscopy image. The second image data may be provided as an overlay of graphical navigation information to the X-ray image, which is indicated in FIG. 2 with a vessels angiogram illustration 118, wherein the angiogram is shown in a dotted manner in the figure to represent that, for example, the display of the angiogram as a roadmap navigation aid can be switched on and off, depending on the second control signal.

The image processing unit 110 is shown as a square box, comprising, for example, a timing unit and a control unit, as described in relation with FIG. 1.

Figure 3:
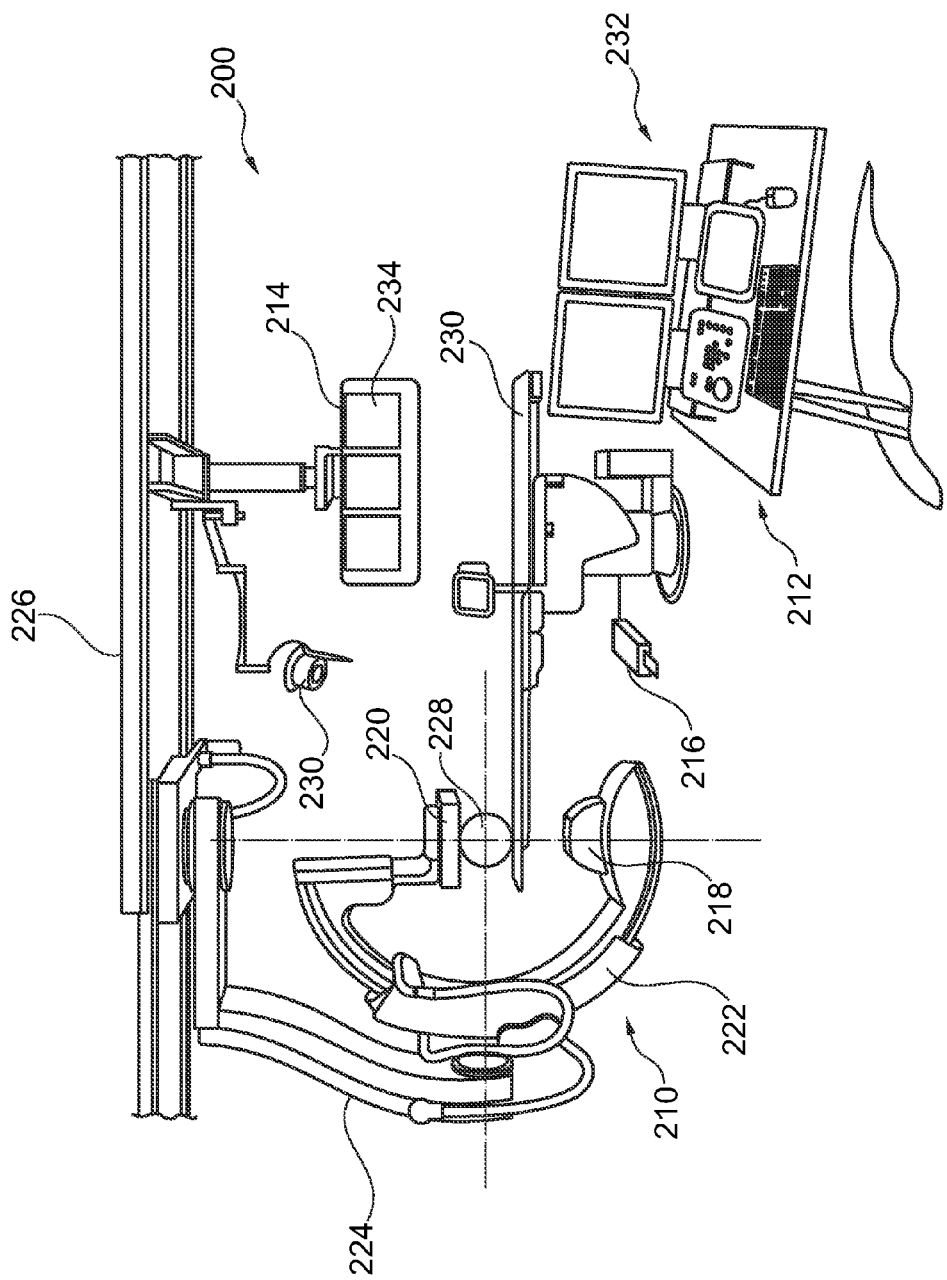
FIG. 3 shows an example of an X-ray imaging system.

FIG. 3 shows an X-ray imaging system 200, comprising an X-ray image acquisition unit 210, a processing unit 212, a display unit 214 and a control interface 216. The X-ray image acquisition unit comprises an X-ray source 218 and an X-ray detector 220. The X-ray image acquisition unit 210 is configured to acquire X-ray image data. The processing unit 212 is configured to generate medical image data. The display unit 214 is configured to present the medical image data. The control interface 216 is provided as a lower limb operable multifunctional interface according to one of the above mentioned examples, for example the lower limb operable multifunctional interface 10 of FIG. 1.

The lower limb operable multifunctional interface provides a first control signal to activate a first function, and a second control signal to activate a second function. The first function comprises an X-ray image acquisition, and the second function comprises an activation and/or deactivation of a display mode.

For example, the X-ray image acquisition unit is provided as a so-called C-arm arrangement, where the X-ray source 218 and the X-ray detector 220 are arranged on opposite ends of a C-arm structure 222, movably supported by a support structure 224, for example mounted to the ceiling structure 226.

Thus, the X-ray image acquisition unit is freely movable around an object 228, for example a patient, provided on a patient support table 230.

It must be noted that instead of the C-arm structure 222, the X-ray image acquisition unit 210 may also be provided as a CT structure, where a gantry is provided for a rotating movement of the X-ray source and the X-ray detector. Further, also other X-ray image acquisition arrangements can be provided, for example moveable and static X-ray image acquisition arrangements.

Further, FIG. 3 also shows lighting equipment 230 and a further user interface in form of a desktop working station 232. Further, the display unit 214 is shown with several display portions showing graphical information 234. For example, the graphical information is provided as graphical user interface, showing different activation areas for controlling different functions. The different functions relate to the at least two different signals of the lower limb operable multifunctional interface, as described above.

Figure 4:
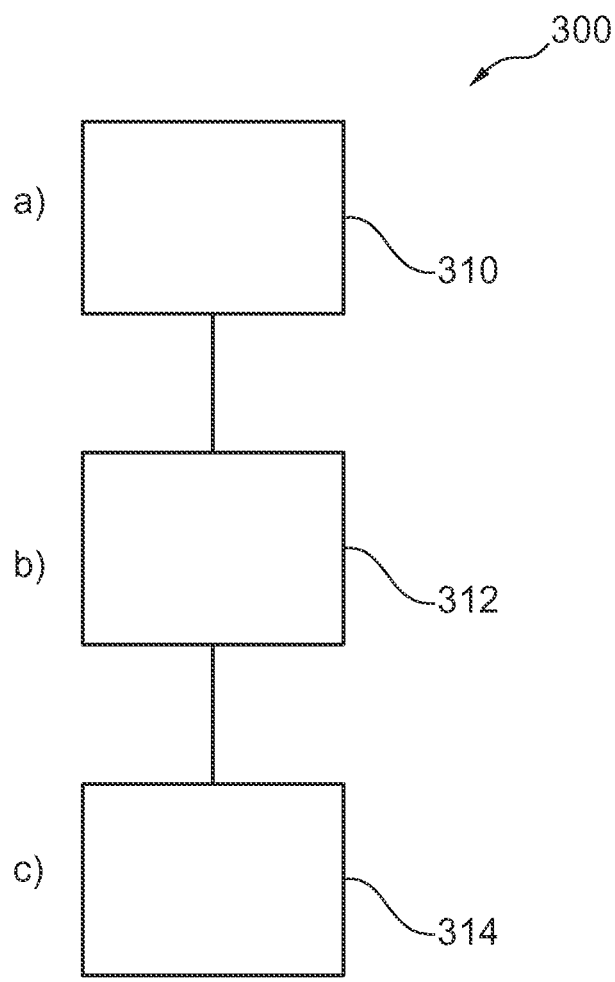
FIG. 4 shows basic steps of an example of a method for controlling an X-ray imaging system.

FIG. 4 shows a method 300 for controlling an X-ray imaging system, comprising the following steps: In a first step 310, an activation signal is generated by pressing an activation element, wherein the activation element is lower limb operable. In a second step 312, a timing signal is provided upon being provided with the activation signal. In a third step 314, at least two different control signals are provided for triggering at least two different predetermined actions dependent on the duration of the timing signal.

The first step 310 is also referred to as step a), the second step 312 as step b) and the third step 314 as step c).

In step a), an activation signal may be generated by pressing at least one activation element, for example a pedal.

According to a further example (not shown), a first control signal is being provided upon pressing the activation element for a first duration, and a second control signal is being provided upon pressing the activation element for a second duration. The at least two different control signals are activating different functions of a medical imaging system. A first control signal may control a first function, and a second control signal is activating a second function. The first function is triggering X-ray image acquisition, and the second function is controlling an activation and/or deactivation of a predetermined display mode.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A lower limb operable multifunctional interface comprising:
    an activation element;
    a timer; and
    a controller,
    wherein the activation element is configured to provide an activation signal to the controller and to the timer when being activated,
    wherein the timer is configured to provide a timing signal to the controller upon being provided with the activation signal from the activation element when being activated,
    wherein the controller is configured to provide at least two different control signals for triggering at least two different predetermined actions,
    wherein the at least two different control signals are dependent on a duration of the timing signal, and
    wherein the at least two different control signals are provided to activate different functions of a medical imaging system.

2. The interface according to claim 1, wherein the lower limb operable multifunctional interface is a foot operable interface, and wherein the activation element is provided as a pedal.

3. The interface according to claim 1, wherein a first control signal of the at least two different control signals is provided upon activating the activation element for a first duration, and wherein a second control signal of the at least two different control signals is provided upon activating the activation element for a second duration.

4. The interface according to claim 1,
    wherein a first control signal of the at least two different control signals is provided to control a first function,
    wherein a second control signal of the at least two different control signals is provided to activate a second function,
    wherein the first function comprises an X-ray image acquisition, and
    wherein the second function comprises one of an activation and a deactivation of a predetermined display mode.

5. The interface according to claim 4, wherein a third control signal of the at least two different control signals is provided upon activating the activation element for a third duration.

6. The interface of claim 4, wherein the predetermined display mode comprises a cardiac navigation application providing navigation aids.

7. The interface according to claim 5, wherein the second control signal activates the predetermined display mode and the third control signal deactivates the predetermined display mode.

8. The interface according to claim 1, wherein two or more activation elements are provided, and
    wherein at least two of the two or more activation elements are each configured to provide different control signals dependent on a duration of activation of a respective activation element of the at least two of the two or more activation elements.

9. The interface of claim 1, wherein the duration of the timing signal is based on a time between starting of activation of the activation element until endpoint of the activation.

10. The interface of claim 1, wherein the activation element is a pressure and a time dependent multifunctional activation element.

11. A lower limb operable multifunctional interface comprising:
    an activation element;
    a timer; and
    a controller,
    wherein the activation element is configured to provide an activation signal to the controller when being activated,
    wherein the timer is configured to provide a timing signal to the controller upon being provided with the activation signal from the activation element when being activated,
    wherein the controller is configured to provide at least two different control signals for triggering at least two different predetermined actions,
    wherein the at least two different control signals are dependent on a duration of the timing signal,
    wherein the at least two different control signals are provided to activate different functions of a medical imaging system,
    wherein the controller is configured to provide an activation signal for X-ray image acquisition when the activation element is activated for a time period longer than a predetermined time, and
    wherein the controller is configured to provide a display mode change signal for changing between at least two different display modes when the activation element is activated for a time period shorter than the predetermined time.

12. A medical imaging device comprising:
an image processor,
a display; and
an interface,
wherein the image processor is configured to generate at least first and second image data,
wherein the display is configured to display the at least first and second image data,
wherein the interface is provided as a lower limb operable multifunctional interface comprising an activation element, a timer, and a controller,
wherein the activation element is configured to provide an activation signal to the controller when being activated,
wherein the timer is configured to provide a timing signal to the controller upon being provided with the activation signal from the activation element when being activated,
wherein the controller is configured to provide at least two different control signals for triggering at least two different predetermined actions of the medical imaging device, and
wherein the image processor is configured to provide the at least first and second image data to the display depending on the at least two different control signals provided by the interface.

13. The medical imaging device of claim 12, wherein the at least two different control signals are dependent on a duration of the timing signal.

14. An X-ray imaging system, comprising:
an X-ray image acquirer;
a processor;
a display; and
a control interface;
wherein the X-ray image acquirer comprises an X-ray source and an X-ray detector, and is configured to acquire X-ray image data,
wherein the processor is configured to generate medical image data,
wherein the display is configured to present the medical image data,
wherein the control interface is provided as a lower limb operable multifunctional interface comprising an activation element, a timer, and a controller,
wherein the activation element is configured to provide an activation signal to the controller when being activated,
wherein the timer is configured to provide a timing signal to the controller upon being provided with the activation signal from the activation element when being activated,
wherein the controller is configured to provide at least two different control signals for triggering at least two different predetermined actions, and
wherein the at least two different control signals are provided to activate different functions of a medical imaging system, and
wherein the lower limb operable multifunctional interface provides a first control signal of the at least two different control signals to activate a first function; and a second control signal the at least two different control signals to activate a second function; wherein the first function comprises an X-ray image acquisition, and the second function comprises one of an activation and a deactivation of a display mode.

15. The X-ray imaging system according to claim 14, wherein a graphical user interface is provided showing different activation areas for controlling different functions, and
wherein the different functions relate to the at least two different control signals of the lower limb operable multifunctional interface.

16. The X-ray imaging system of claim 14, wherein the at least two different control signals are dependent on a duration of the timing signal, and wherein a parameter for determining the duration of the timing signal is determined by counting a number of incoming X-ray images incoming from the X-ray acquirer.

17. The X-ray imaging system of claim 14, wherein the display mode comprises an overlay of an X-ray image with a vessel roadmap, the vessel roadmap being an angiogram.

18. A method for controlling an X-ray imaging system, comprising acts of:
generating an activation signal by activating an activation element, the activation signal being provided to a controller and to a timer;
providing a timing signal to the controller via the timer upon the timer being provided with the activation signal from the activation element when being activated; and
generating via the controller at least two different control signals for triggering at least two different predetermined actions dependent on a duration of the timing signal,
wherein the at least two different control signals are provided to activate different functions of a medical imaging system.

19. The method according to claim 18, wherein a first control signal of the at least two different control signals is being generated by the controller upon activating the activation element for a first duration, and wherein a second control signal of the at least two different control signals is being generated by the controller upon activating the activation element for a second duration.

20. A non-transitory computer readable storage medium containing a computer program element stored therein for controlling an apparatus which, when being executed by a processor, configure the processor to perform acts of:
causing generating of an activation signal by activating an activation element, the activation signal being provided to a controller and to a timer;
causing providing of a timing signal to the controller via the timer upon the timer being provided with the activation signal from the activation element when being activated; and
causing generating of at least two different control signals via the controller for triggering at least two different predetermined actions dependent on a duration of the timing signal,
wherein the at least two different control signals are provided to activate different functions of a medical imaging system.

* * * * *